Figure 4:
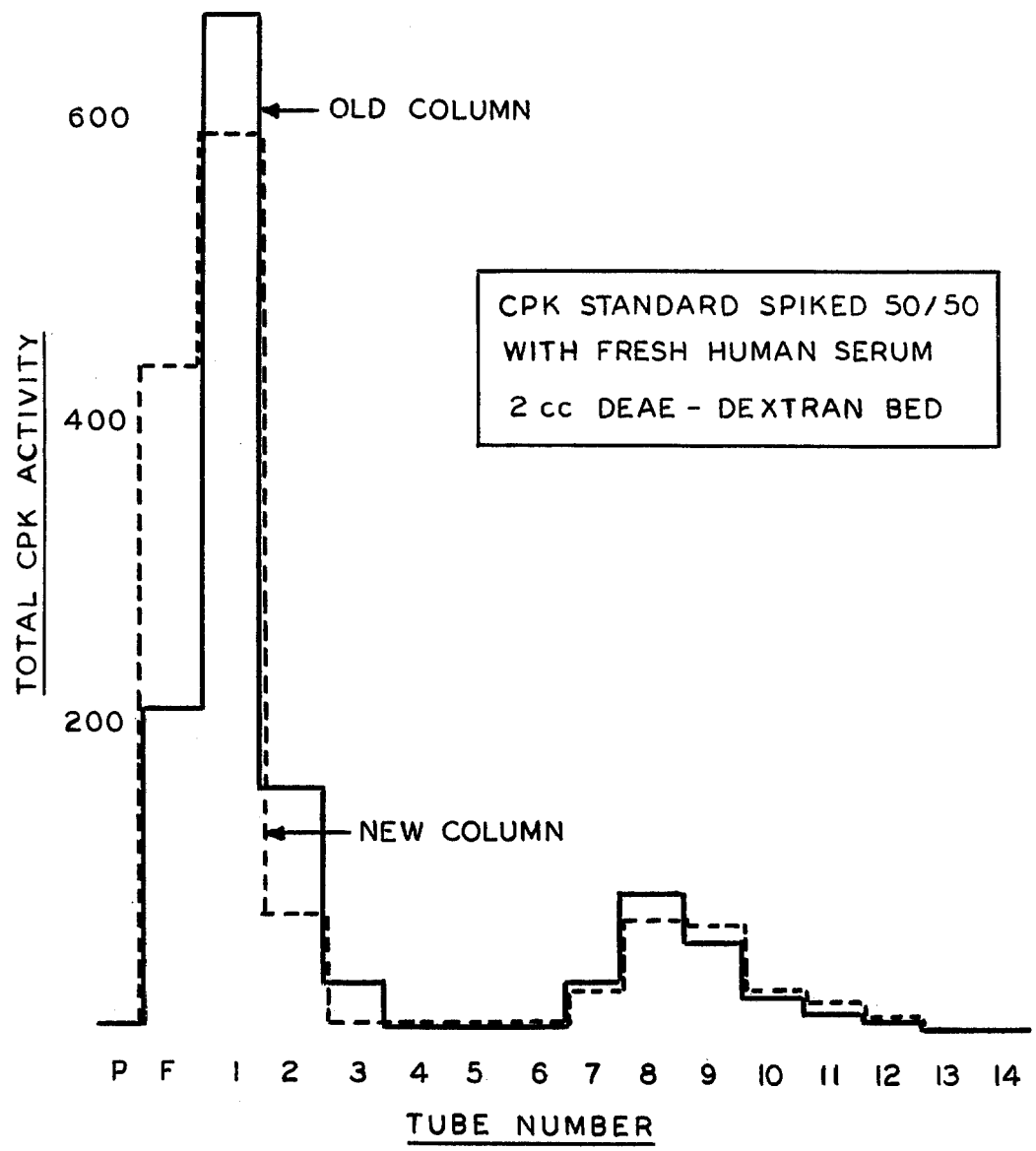

United States Patent [19]

Kiyasu

[11] 4,105,499

[45] Aug. 8, 1978

[54] HEART ATTACK SCREENING METHOD, APPARATUS AND KIT FOR SAME

[76] Inventor: John Y. Kiyasu, 94 Meadow St., Garden City, N.Y. 11530

[21] Appl. No.: 730,102

[22] Filed: Oct. 6, 1976

[51] Int. Cl.² ............................................. G01N 31/08
[52] U.S. Cl. .............................. 195/103.5 R; 195/127
[58] Field of Search ................... 195/103.5 R, 68, 127; 210/198 C

[56] References Cited

U.S. PATENT DOCUMENTS

| | | | |
|---|---|---|---|
| 3,179,587 | 4/1965 | Battista et al. | 210/198 C |
| 3,562,289 | 2/1971 | Battista et al. | 210/198 C |

OTHER PUBLICATIONS

Mercer, Clin. Chem. vol. 20, No. 1, (1974), pp. 36–40.
Klein et al., Clin. Chem. vol. 23, No. 3, (1977) pp. 504–510.
E-C Bulletin, vol. VIII, No. 1 (1976), E-C Apparatus Corporation.
Morin, Clin. Chem. vol. 23, No. 2, (1977), pp. 205–210.
Dixon et al., "Enzymes" Academic Press Inc., Publishers, New York (1964), pp. 43–44.

*Primary Examiner*—Alvin E. Tanenholtz
*Assistant Examiner*—C. A. Fan
*Attorney, Agent, or Firm*—E. Janet Berry; Lawrence Rosen

[57] ABSTRACT

A diagnostic method for the rapid detection of heart attacks in human patients which comprises passing patient blood serum through a chromatographic column, isolating and identifying the major portion of creatine phosphokinase-MB isoenzyme from the eluate by the inclusion of a green food color. The column may be recycled and reused.

9 Claims, 6 Drawing Figures

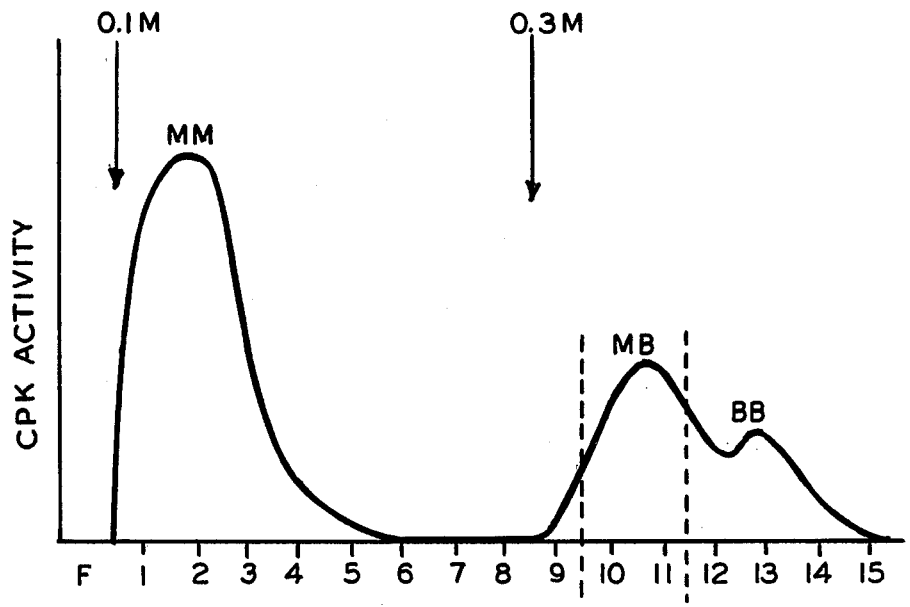
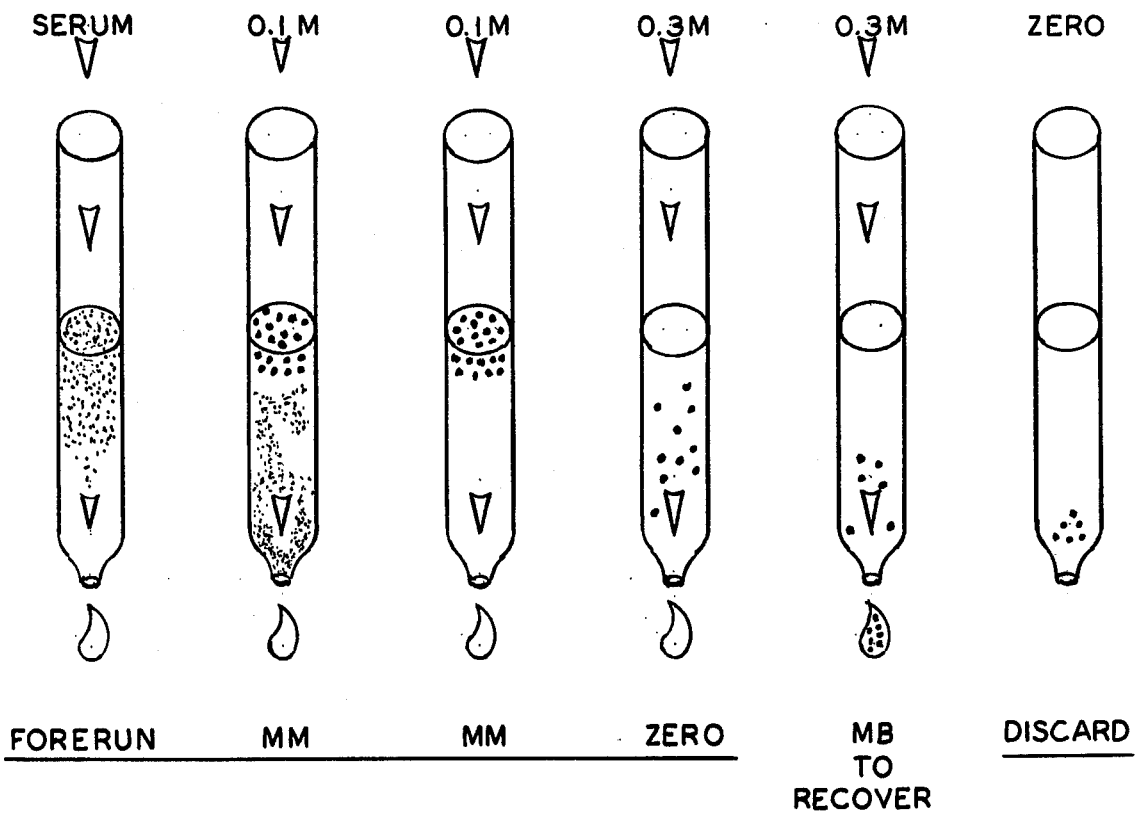

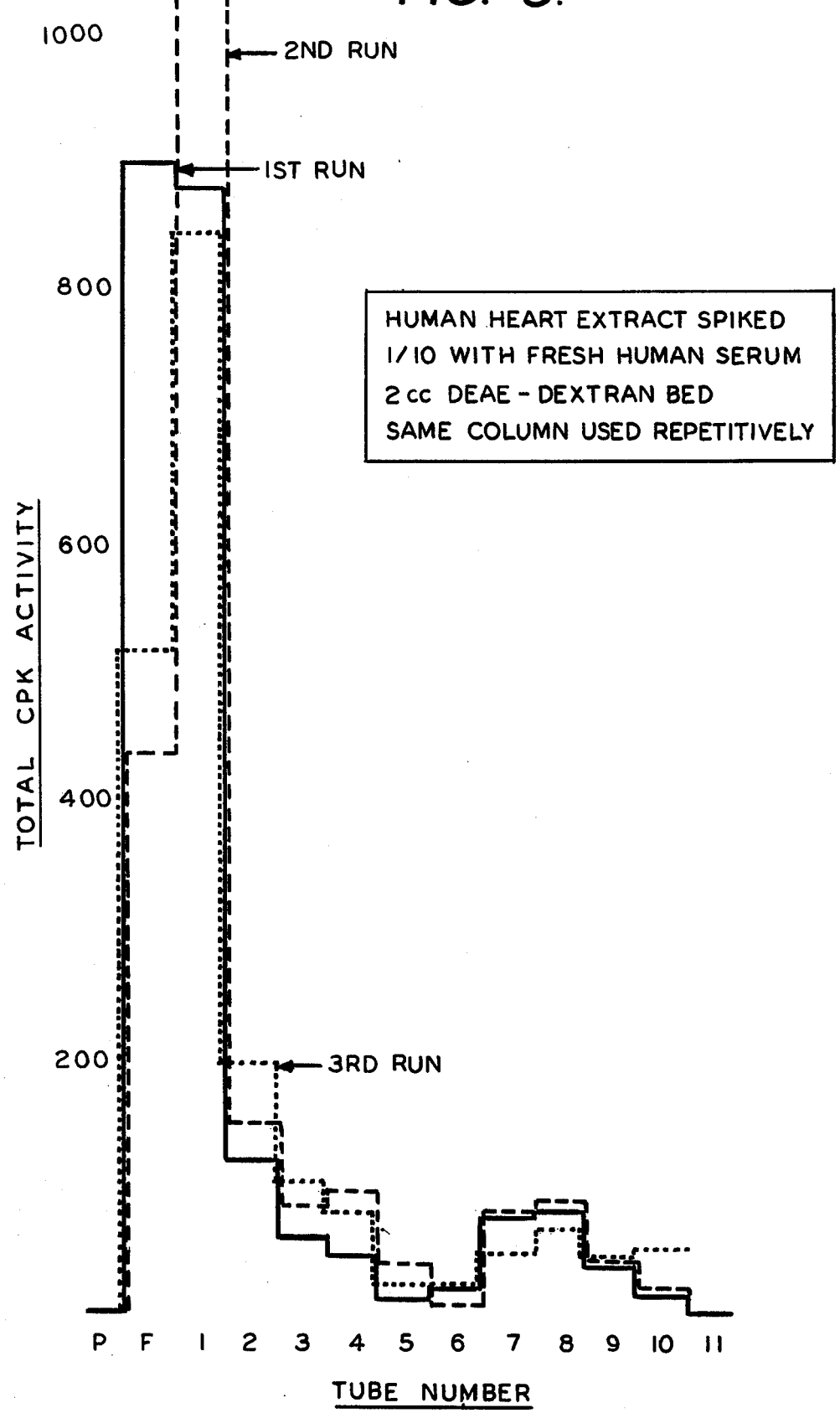

CONTINUOUS FLOW ANALYSIS OF CPK-MB
(AUTO-ANALYZER TECHNIQUE)

CPK STANDARD SPIKED 50/50 WITH FRESH HUMAN SERUM 2 cc DEAE-SEPHADEX A-50 CARTRIDGE CHROMATOGRAPHY BY CONTINUOUS FLOW

HEART ATTACK SCREENING METHOD, APPARATUS AND KIT FOR SAME

The invention consists generally of a modified apparatus and especially a kit packaged method and apparatus for isolating, identifying, and quantitatively measuring the MB iso-enzyme of creatine phosphokinases in fresh human blood serum.

It has been known and practiced in the past to make a quantitative separation of the three iso-enzymes of creatine phosphokinases (CPK) by either electrophoresis or anion-exchange chromatography. They are separated into three separate entities: CPK-MM, MB, and BB. The MB fraction of creatine phosphokinases has generally been expressed as a percentage of the total CPK in human serum. The determination and finding of CPK-MB in human serum is almost completely indicative of the condition called myocardial infarct, otherwise and commonly known as a "heart attack" in the patient.

The column separation of the three iso-enzymes of creatine phosphokinases (CPK)—by anion-exchange chromatography for routine clinical laboratory use—has been found to have a number of difficulties which include the following:

1. High speed columns made of DEA-glass beads although effective in isolating the cardiac fraction (MB) are quite expensive for routine testing. Therefore a 1.5 ml. column which is generally not considered regenerable (re-usable) becomes a considerable cost disadvantage.
2. Columns made of DEAE-dextran (polyglucose polymer glucose) effective for the process except that the flow rate is slow, and furthermore they are compressible such that hand pressure using hand bulbs, for example, result in compaction and further slowing of the flow-rate.

It has been found that by using columns of several commercially available anion-exchangers such as DEAE-dextran or DEA-glass beads together with certain elution buffers, the CPK-MB can be isolated predictably, reproducibly and proportionately. The fractions are isolated in a form sufficiently concentrated that the CPK-MB activity may be determined on this eluate thereby proving clinical data completely consistent with the condition termed myocardial infarct and the results indicate suggested degrees of infarct size (severity of the "heart attack"). The simplicity of the invention procedure is such that different technologists can obtain essentially identical results on a given blood serum specimen.

In general, the invention includes the following features:

1. The isolation procedure, including the order of elution buffers with emphasis on a "priming" step before introduction of the MB fraction. A method for preparing a suitable laboratory control for CPK-MB is also included as a necessity.
2. A hybrid column, having both high speed (through-put rate) and low cost of matrices.
3. A non-cloggable spigot plug to replace others which are usually of the fritted plastic or glass disc type. The material preferred is a 5 mm. slug of a filter tip as used in conventional filter type cigarettes.
4. New column matrices in which a 30 mm. × 10 mm. slug of DEAE-cellulose "filter tip" comprises, if desired, the entire internal core of a CPK column.
5. The design and chassis of the CPK column, with description of suitable racks for use in conjunction with said columns in a clinical laboratory.

Using a combination of DEAE-dextran and DEA-glass beads, a completely satisfactory column can be made requiring only 0.25 ml. of DEA-glass beads. A similar high density matrix such as inert glass beads or reagent grade sea sand can be used in place of the DEA-glass beads.

DEAE-dextran is a high capacity anion exchange dextran polymer of relatively low density. DEA-glass beads, sea sand, or inert glass beads are high density non-compressible matrices. A hybrid column made of low density dextran and one of the indicated non-compressible materials in a suitable buffer behaves very predictably for the test. Upon inversion of the column by a simple hand rotation the sand or beads consistently layers to the bottom of the column effectively shielding the porous retainer of the column. Since the DEAE-dextran is layered on the upper most portion of the column bed, the flow rate can readily be speeded by the application of the hand bulb. If the column is found to be very slow this defect is readily correctable by the application of suction or partial vacuum on top of the column by the same hand bulb. The back suction applied to such a column serves to lift the bed matrices off the porous column retainers thus freeing small dextran particles from the retainer. Upon compression of the bed with the same hand bulb, the more dense sand or beads settles first and serves as a non-compressible "porous" barrier thereby preventing clogging, channeling and other undesirable effects in the column.

There are special advantages in using columns of certain design, size, and type. In addition to the fact that the columns should be of a convenient and easily useable size, both in length and diameter, it is also important that these columns be readily transportable by conventional carriers, readily stackable in package form thus occupying minimal bulk storage space, and readily inspected for any matrix defects (air bubbles, bacteria, and the like).

Each column has the same bed capacity so that the elution protocol will result in reproducible recovery of the CPK-MB fraction. In addition, for routine clinical laboratory analysis, a 1.5 ml. aliquot of serum is a highly useful aliquot since conventional sample cups used in autoanalyzers for serum, and other samples are in fact designed for 1.5 ml. samples. Thus, the bed capacity of the column, the elution characteristics, and the like should be designed around this load capacity as closely as possible.

The column matrix for use within the selected columns should be of such size and material that high flow rates are maintained to give both speed in performing the test as well as accurate and reproducible results. For adoption as a practical clinical tool, the matrix should also and preferably be composed of readily available materials of relatively low cost.

A diethylaminoethane derivative of dextran suitably cross-linked and commercially available (i.e. PharmaciaSephadex A-50, etc.) is prepared by hydrating directly into Solution #1 (0.1M NaCl, 0.05 M "Tris", 0.1% sodium azide, 0.016 M dithiothreitol, pH 7.9). This slurry is made by gentle stirring with sufficient buffer so that upon settling of the anion exchanger an equal volume of supernatant liquid is available to the bed volume. This swelling and hydration step is allowed to age at least several days at 4° C before the suspension is used for pipetting into empty columns. After the aging period, the anion-exchanger suspension is brought to room temperature and approximately 5 ml of the hand-stirred slurry is pipetted into each column. The approximate volume of the resin should be 2.5 ml per column. This bed volume-when compacted, however, by buffer flow through the column, or by hand bulb pressure, effectively becomes a 2.0 ml bed volume.

The above column may be fitted with a sintered disc or fritted disc or a 5 mm. cigarette filter tip. The column flow matrices may be improved by the addition to this column of 0.25 ml. or reagent grade sea sand, inert glass beads (such as "Super Brite" beads, etc.) or DEA-glass beads (Corning).

The procedure for isolating a slug of the CPK-MB fraction is based on the use of only two eluting buffers, i.e. herein identified as Solution #1 and Solution #2. The composition of the above are the following.

Sol #1 0.05 M "Tris", pH 7.9, 0.1 M NaCl, 0.016 M DTT and 0.1% sodium azide

Sol. #2 0.05 M "Tris", pH 6.9, 0.3 M NaCl, 0.016 M DTT and 0.1% sodium azide.

The elution with Solution #1 quantitatively removes all of the CPK-MB fraction, resulting in absolutely no carry over into the MB slug. The prime step, in fact, assures this (1 ml of Solution #2). Upon changing to a clean collection tube—the "peak slug" of the CPK-MB fraction is obtained—by eluting the column with 2.0 ml of Solution #2. The purpose of this is two-fold as follows:

1. An MB fraction devoid of MM carry over.
2. An MB fraction of sufficiently high concentration.

By fulfilling the two above conditions, both selectively and sensitivity are obtained. Under the conditions of the test, the "2 ml" Solution #2 eluate may be examined either by electrophoresis or by simply assaying for CPk activity using the so-called Rosalki substrate. A typical prescribed procedure is ideally suited for the Beckman TR Enzyme Analyzer, the Dupont ACA, or performed manually on the Gilford 300-N, or using any other suitable instrumentation. The overall procedure should not take more than one-half hour, including spinning down the clotted blood and will require a minimum of 15 minutes for a total turn-around time.

The procedure is sufficiently sensitive to detect a myocardial infarct one half hour after onset—on a total CPK serum activity of 200 mIu/ml. This means that the procedure is sufficiently sensitive to be used as an admission index in an emergency room or special care service.

The clear glass columns are readily inspected for entrapment of air bubbles or any other irregularities. Air bubbles are easily removed by gently inverting the columns several times. The procedure is as follows:

Step 1. Remove the top cap first, the remove the spigot nipple. Allow the supernatant liquid to drain through by gravity.

Step 2. Assay patient serum for total CPK. If the activity is greater than 200 mIu/ml, proceed as below. Otherwise request another patient specimen—if so desired.

Step 3. Transfer 1.5 ml of patient serum into the column bed. Allow serum to drain through bed by gravity.

Step 4. Wash column with 2 or 3 aliquots of 4-5 ml of Solution #1. Three aliquots are recommended when the total CPK is greater than 1000 mIu/ml.

Step 5. Prime the column with exactly 1.0 ml. of Solution #2.

Step 6. Change collection to a clean test tube.

Step 7. Elute column with exactly 2.0 ml of Solution #2 and assay this eluate for CPK activity.

Since the eluate of Step 7 above represents the MB fraction—this CPK activity is expressed as an absolute value.

An MB signal of 4 mIu/ml is considered negative, 5 mIu/ml is considered questionable. Anything greater than 5 mIu/ml is considered positive for myocardial infarct.

If the technologist or any other personnel is in doubt with the result, the assay or the MB fraction can be repeated. If the doubt is still not resolved, another aliquot of the same serum should be processed through the same column procedure on another, unused, column. The ultimate degree of doubt should result in drawing another blood specimen, that is, from the same patient. In the acute phase of myocardial infarct—the CPK-MB signal will not only remain—it will tend to get higher and peak dramatically at approximately 12 hours after the heart attack. The MB signal generally is no longer detectable 48 hours after the myocardial infarct.

Proper quality control requires that all technologists on different shifts, day or otherwise—compare results based on processing the same specimen. If Solution #2 is used instead of Solution #1, for example, completely erroneous results will occur. Thus Solution #1 is color coded for instance green and Solution #2 (a smaller bottle) is color coded for instance orange. The use of food coloring (green) may be dissolved in the Solution #1 to further prevent cross contamination of each respective solution. The recommended dosage is 1 drop of green to 1 liter of Solution #1. Pipettes may also be so color coded with colored tapes—in order to avoid cross contamination, and if this is done the same pipette may be used over and over again. These solutions and columns are "preserved" by the use of 0.1% sodium azide and have been used, opened, closed, repeatedly at room temperature (20°-30° C) for long periods of time with no deleterious effects. However, if any sediments, opaque clusters or the like which may be suggestive of microbial growth, is evident the solution or column must be discarded. Frequent checking the buffers for proper pH is recommended.

The use of rubber hand bulbs are highly recommended not only for pipetting serum solutions, but also for applying pressure or suction to the column during Step 4 when the MM fraction of CPK is being washed out. The efficacy at Step 4 is only for speed and the hand bulb technique can be omitted if time is of no urgency. It is highly recommended that these columns be discarded after use, or recycled only in accord with a given procedure as a precaution against hepatitis, and other undesirable results. These columns have been designed not only for accuracy, precision (reliability) but also with regard for cost. Thus, they provide high quality analytical results but are truly disposable.

Experiments designed for defining the elution characteristics, separation, recovery, and other details reveal the following:

(1) Upon the addition of 1.5 ml. of fresh human serum onto this column, and after wash out with two (4-5 ml) aliquots of Solution #1, 100 percent of the MM fraction is removed from the column. A third aliquot of Solution #1 simply assures the absoluteness of this wash out procedure.

(2) The "priming" step of 1 ml of Solution #2 begins to bring out the fore-shoulder of the MB fraction and has a low MB signal.

(3) The final collection elution of 2 ml of Solution #2, brings out the slug of MB peak with a good signal for CPK measurement. The use of green (food color) in Solution #1 results in the elution of the green pigment with Solution #2 in this same MB fraction, and is therefore a desirable visual marker for the MB fraction. This green pigment in no way interferes with the CPK-MB assay when using the Rosalki procedure.

(4) This MB fraction constitutes approximately 70 percent of the total MB fraction with considerable consistency since both shoulders of the peak are involved.

(5) Up to 10 percent of the BB fraction may be recovered in the MB fraction, but this does not cause any diagnostic problems since the absolute BB signal is quite low in adult human serum even in subjects suffering from renal impairment.

Controls:

In addition to inter-technologists performance controls as above described, it is recommended that a known CPK standard of established isoenzyme composition such as is used in electrophoresis be used daily for column analysis. Instead of adding 0.5 ml or 1.0 ml of distilled water as in the direction for electrophoresis analysis, such standards may be reconstituted in 16 ml of 0.01 M phosphate buffer of pH 7.4 to which is added 7 drops of 10 percent DTT (dithiothreitol). This solution is stored in the refrigerator overnight in order to assure the re-activation of inactivated BB and MB. The mixture is then generally stable for 10 working days allowing ten 1.5 ml aliquots for use as column analysis controls.

The second and most important control is performed electrophoretic analysis of the column MB fraction. A MB signal of 20Iu/ml can be readily analyzed by agarose-Rosalki-fluoremetric analysis if 4–5 ul of specimen is applied on the gel or if the entire MB eluate is concentrated (i.e. Amicon, or similar concentrator) approximately ten fold, and applied conventionally with a micro-applicator.

It is important to note that CPK-MB and BB is readily oxidized when admixed with other disulfide containing proteins, and has caused considerable controversy among different laboratories and investigators.

Therefore, it is important to emphasize the need to use highly recommended CPK isoenzyme standards (i.e. Helena Labs, etc.) and furthermore to recognize that such standards, even when obtained from the same manufacturer may show lot-to-lot variability.

Reagents

Columns

These columns are designed for clarity (visual observation), flow and wash out design, quality control especially as related to uniform bed volume, and disposability. The diethyl-amino-ethyl dextran is thoroughly hydrated, aged and stabilized with a bacteriostatic preservative. The column is already equilibrated in buffer #1 and is ready to be used in a stand-by mode. In the event a particular column is drained but not actually used, the addition of buffer Solution #1 and the re-capping of the column, results in the original storage form.

Buffers

Solution #1 and Solution #2 are packaged in a 10 fold concentrated form. Each 20 ml vial must therefore be diluted with 180 ml of deionized or distilled water. Appropriate color coded labels are inserted for use in properly labelling the working solutions.

Unopened packages may be stored in the refrigerator (0°–4° C), however, opened kits should be kept at room temperature.

Stability

Columns and kits packaged for the method may be stored at 0°–4° C for a period of one year and opened packages at room temperature for a period of three months.

Specimen collection

Clotted blood samples obtained in venipuncture collection tubes are adequate. Hemolysis does affect thetotal CPK activity (increase) when assayed using the Rosalki substrate but does not at all affect the MB fraction. Serum should be left on the clot and refrigerated wherever possible. The glutathione reductase of red blood cells presumably maintains a redox environment suitable for MB stability. Serum separated from the clot should be assayed within 4 hrs. when kept at room temperature. It is believed important to keep the serum on the clot and refrigerated, if the MB assay is not immediately performed. Wherever at all possible the use of fresh human serum is recommended.

Procedure

CPK assay

The use of the Rosalki procedure is recommended in view of its sensitivity and reliability. Myokinase, when present, will give a false high total CPK. However, myokinase is not at all recovered in the MB fraction and therefore does not interfere with the signal. Also recommended is the use of instrumentation at 37° C employing zero-order kinetics, whether manual or automated. This recommendation is made because of the fact that different specimens have different degrees of lag phase, therefore, fixed point readings may create artifacts and values based primarily on differences of lag phase.

CPK as an Enzyme

This enzyme is a dimer, with no catalytic activity when it is present as a monomer and/or in the disulfide form. The BB and MB fractions are more readily oxidized than the MM isozyme although all can eventually be oxidized and therefore inactivated. Since sera and tissue extracts have many disulfide proteins (albumins, globulins, and the like), it is understandable that different investigators and different laboratories have produced much conflicting reports. Extreme caution must be observed because of the sulfhydryl-disulfide interchange and judicious handling of sera and controls must be employed. CPK Standards generally used for electrophoresis are probably the best controls. Such "protein-free" controls may be "spiked" with fresh human serum for column procedure control. Sera from pregnant females are found generally low in total CPK activity but any other fresh serum of low CPK activity must be used as a suitable base.

These columns are extremely efficient and perform equally well with low or "normal" protein concentration. However, it is recommended that column controls should mimic as closely as possible the unknowns (fresh human sera).

Rack

The test rack was designed to occupy minimal bench space, as well as to provide clarity, specimen indentity and minimal cross contamination. Therefore the column spigots are "free-hanging", sufficiently high to prevent back-splashing, and yet generally with a low center of gravity. The collection supports actually may serve as a sample tray again facilitating specimen identification. The plastic sheets are laminated wherever possible for structural support and should be cleaned only with cold tap water either under the sink faucet or using a clean wet cotton gauze. The rack should be cleaned once a day in order to minimize sera contamination and for general hygienic purposes. This rack is quite expensive and should be so handled as valuable property.

Note: two holes are reserved for pipette Solution #1 and Solution #2. These pipettes should be color taped so that they will only be used with their respective bottles. Mouth pipetting should be discouraged wherever possible. Disposable 5 ml Mohr pipettes with a cotton plug are recommended for routine use. The receptacles are so designed to house them. Solution #1 and Solution #2 may be substituted by other salts such as potassium chloride, sodium bromide, potassium bromide, and the like of equivalent ionic strength. The optimum molar concentrations of these salts may vary depending on their effective ionic strength. The particular salts and buffers employed in the Examples are selected for convenience as they are routine laboratory reagents.

The materials do not generally require any special handling as they are also selected to avoid fragmentation and/or friability. However, they should be handled with such care so as to avoid causing excess bubble entrapment into the column matrices. Such entrapments are readily removed by repetitive inversion of the column.

The spigot is a further important portion of the column and it has been discovered that a 5 mm. plug made from the filter tip of a commercial cigarette can be used quite satisfactorily for this purpose. These filter tips are generally made from linearly milled cellulose fiber of controlled porosity designed for prescribed flow characteristics (for instance inhalation). Cigarette filter tips from all brand name cigarettes tested thus far have been found to be perfectly suitable.

Thus one embodiment of the invention and one which is especially adaptable for packaging, storage and distribution in kit form is made from DEAE-dextran, sea sand (reagent grade) and the commercial cigarette filter tip employed in combination. Such an assembled device has been found to provide both fast flow and also high analytical accuracy and reproducibility when used in CPK-MB determinations in fresh human serum.

Analytical columns, especially in the clinical service environment, are generally not considered re-usable. In the case of anion-exchange columns, a number of matrices after repeated use, begin to disintegrate physically and also, to some extent, co-valently. Their selectivity changes slightly, but sufficiently, to alter elution patterns with diminished separation of component fractions.

The DEAE-dextran is perfectly stable when treated with Solution #1 or Solution #2 and fresh human serum—such that these columns can be used repetitively through the procedure. In fact, careful elution of a fresh human serum containing known composition of the three CPK isozymes (MM, MB, and BB), repetitively, on the same day or on subsequent days results in the same elution patterns and with consistent and satisfactory MB resolution.

It is thus possible to use the DEAE-dextran cartridges in "closed" systems employing continuous flow analytical techniques. Since DEAE-dextran is a compressible matrix, this cartridge was used proximal to the proportioning pump, in which "reduced" pressure is applied to the cartridge. The elution protocol is identical to the column procedure: Serum–Solution #1–Solutions#2.

The above advantages make routine applications even simpler in that re-usable columns can be used in physicians offices in dip-stick fashion, and in technique-free procedures in busy automated clinical laboratories. The number of repetitive runs on one column has not been exhaustively evaluated but it does appear that at least 10 consecutive runs can be made on a column or cartridge before discard is necessary, thus reducing cost, and providing other advantages. The use of a DEAE-cellulose filter tip cartridge either for column or continuous flow for the techniques described above are obvious. It is also necessary in repetitive (recycle) use that the samples processed, in reusable columns, be non-hemolyzed, clear and free of jaundice (as a matter of precaution).

Steps in Regeneration of a column/cartridge:

(1) after a MB run, pass through 10 cc. of additional Solution #2.
(2) for opitmal equilibration, pass through 5 cc. of Solution #1.
(3) the DEADE-dextran column or cartridge is as good as and equivalent to its original condition.
(4) the cartridge should be designed symmetrically in order to minimize compaction; the polarity is changed, that is, the inlet becomes the outlet, by simply inverting the cartridge by disconnecting and reconnecting to the pump tubes.

The invention will further be described and illustrated by the following specific examples. However, it is in no way intended to limit the scope and parameters of the invention thereto.

EXAMPLE 1

In carrying out the procedure of the invention, a commercially available DEAE-dextran columns from E-C apparatus or a prototype column such as obtained from Hofmann LaRoche may be used with attached and modified elution buffers. A bed volume of 1.5 ml. of DEA-glass beads is used and the beads must be individually poured into th column. Glass or dextran (2 ml bed capacity) columns are equilibrated in 0.1 M NaCl (sodium chloride) containing 0.05 M "Tris" buffer of approximately pH 7.9. More particularly, the top cap of the column is first removed followed by removal of the bottom spigot. The excess buffer is there removed by gravity flow or, if desired, from the supernatant liquid using a Pasteur or similar pipette. If the freshly obtained human serum has a total CPK activity of 200 Iu/liter or greater, 1.5 ml. of this serum is transferred onto a column prepared as described above. When the serum has completely passed through the column bed, the column is washed with two or three aliquots of a first solution (0.1 M NaCl, 0.05 M "Tris" pH 7.9 using about 4–5 ml. per aliquot. The column is then primed with 1 ml. of a second solution (0.3 M NaCl, 0.05 M "Tris", pH 6.9). The MB fraction is then collected in a clean test tube by washing the column with the following indicated aliquot of the second solution 2 ml. for DEAE-dextran column, and 1 ml. for the DEA-glass bead column. The eluate obtained is assayed for CPK-MB.

FIG. 1 and FIG. 2 respectively present pictorial descriptions of the procedure, by means of a plot of the CPK acitivity vs. it elution characteristics and by means of a successive series of tubes show the CPK-MB fraction as it moves down the tube during the procedure.

If this fraction is found to have a CPK activity of 5 or less (Iu/liter), the specimen is considered negative for infarct.

A CPK activity greater than 5 (Iu/liter) is considered positive for infarct, that is, provided all the clinical symptoms in the patient are consistent with a myocardial infarct condition.

A suitable control for the abov procedure is carried out by using the CPK-isoenzyme standard prepared conventionally for electrophoretic analyses. Such an appropriate control is the Helena laboratory CPK-isoenzyme standard. One vial of this preparation is diluted with 16 ml. of 0.01 M phosphate buffer, pH 7.4, to which is added 7 drops of 10 percent DTT (dithiothreitol). Such a control prepared as above described can generally be used for a period of 2 weeks if it is stored in the refrigerator. It should be put through the entire analytical procedure to establish that the overall process is working predictably and reproducibly before its use on patient serum.

EXAMPLE 2

The formulations of the following bed matrices are designed for the processing of 1.5 ml. of fresh human serum and are comparable in use to the 1.5 ml. bed volume column made of DEA-glass beads or the 2.0 ml. bed volume column made of DEAE-dextran as described above in Example 1.

The DEAE/DEA bed: 0.75 ml. DEAE-dextran / 0.25 ml. DEA-glass beads mixed and hydrated in a suitable buffer.
  The DEAE/Sand bed: 0.75 ml. DEAE-dextran / 0.75 ml of reagent grade sea sand or inert glass beads and hydrated in suitable buffer.

Commercially available DEAE-dextran columns from E-C Apparatus or commercial proto-type column can be made "fast" by adding dry glass beads or sand to the existing hydrated columns. The proportion and volume of the hybrid columns described above are designed to replace the mono-bed columns of either DEAE-dextran or DEAE-glass beads, suitable for precessing 1.5 ml. of human serum.

In Example 1 above columns made of hybrid matrices were described for the purpose of achieving high flow rates and low cost material matrices using a comination of DEAE-dextran and reagent grade sea sand or inert glass beads. The other important part of a column is the spigot or retainer which retains the column bed or matrices but without unduly slowing the flow rate.

Conventional columns have, as a retaining septum, either a plug of glass wool, a fritted or sintered glass or a plastic disc or plug. Ordinary cigarette filters such as those attached to the cigarette bodies of commercial brand filtered cigarettes function quite well as disposable plugs and are usable in conjunction with both the hybrid Dextran-Sand columns and the Dextran-Glass Bead columns. The fritted retainers of commercially available columns from E-C Apparatus or a commercial proto-type column are removed and replaced with a 5 mm. plug of the filtered tip of a commercial brand filer cigarette. The plug of the filter tip is then inserted into the spigot receptacle and is covered with 0.5 ml. of sea sand or glass beads. A hydrated 0.75 ml. aliquot of DEAE-dextran in an appropriate buffer is then delivered to the column and a cap is place on both top and bottom of the column. After repeated inversions, and after all trapped air bubbles have been removed the sand or glass beads is layered directly above the filter plug and finally layered by the DEAE-dextran. Such a column design shows extraordinary flow rates and behaves well even with compression or decompression.

The cigarette filter plugs presumably work better than fritted or sintered discs in that they provide a linear flow (parallel channels of the fiber matrix), and also serve as a slightly elastic cusion allowing the total column matrices to respond to hand bulb compression or decompression. A further advantage for the use of cigarette filter plugs is that the unit cost per column part becomes quite minimal and thus allowing for the design of a truly disposable analytical column. Finally, a linear filter plug, as provided in the filters of filtered cigarettes have sufficient structure so as not to collapse, or plug up and thus result in higher flow rates. Thus a 0.75 ml. DEAE-dextran/0.5 ml. sea sand or glass bead/5 mm. linear filter plug hybrid column has been designed for high speed analytical work especially suitable for the STAT determination of CPK-MB in fresh human serum.

EXAMPLE 3

In clinical laboratory work two sizes of test tubes are commonly available and used, i.e. 16 mm × 100 mm. or 13 mm. × 100 mm. These sizes are the same as the Vacu-tainers or the containers used for blood collection which are regularly of these two sizes. It is therefore convenient to design a column chassis, which incorporates these two sizes. Since the 13 mm. (O.D.) tube fits very nicely into the 16 mm. (O.D.) tube, a column chassis can easily incorporate these two diameters. The incorporation of these two sizes also provides a number of functional advantages as will be more apparent in the following detailed description.

The upper portion of the column chassis as illustrated in FIG. 1 has an outer diameter of 16 mm. and is 50 mm. in height. Continuous to this upper portion the bottom portion of the column chassis will be 13 mm. in outer diameter and 30 mm. in length. The inner diameter of this lower portion will be 10 mm. The shoulder provided by joining the 16 mm. to the 13 mm. cyclinders will provide two functions:

1. The shoulder provides a means by which the column will seat firmly in the holes provided in a rack or in the absence of a rack, and allows this column to sit directly into a receiving 16 × 100 or 16 × 150 test tube.

2. The lower (10 mm I.D.) portion of the column will serve as the receptacle for the column matrices whereas the upper portion of the column (16 × 50) will serve as a reservoir for the eluting buffer.

Another ancillary function of this column chassis design is the fact that this conformation allows the stacking of empty columns one into the other thus simplifying and making compact packages suitable for mailing and storage. Finally, the meniscus of the 16/13 junction will serve as a useful marker of bed volume size, both for the manufacturer and the user, in terms of quality control, since the elution pattern of a column is a function of elution volume and also matrix bed size (volume).

Finally, this special column design allows the spigot of the column to "hand-free" especially when used in a rack assembly, since the 16/13 junction will secure the column suspension.

The spigot design is shown with both an inner and outer spigot design. The spigot with shoulders for outer surface of the 13 mm. cylinder allows for "unobstructed" interior flow. The spigot with shoulders designed for the interior walls of the 13 mm. cylinder has the following desirability:

1. The column design is more visually attractive and also minimizes obstruction when it is inserted into the holes of a rack or into a 16 × 100 or 16 × 150 recipient tube.
2. The interior spigot has a receptacle for a 5 mm. filter plug, as well as a 0.5 ml. aliquot of sea sand or inert glass beads. This same receptacle can be used to house a portion of DEAE-filter tip cartridge, if desired.

A suitable rack design, as illustrated in FIG. 2 preferably has one row of holes. The rack hangs rather low thus preventing the need for a wide base (center of gravity), and occupies minimal bench space. The ⅛ inch plexi-glass or otherwise transparent plastic is essentially three separate linear pieces shaped into a C-shape on its side with the back of the C serving as the horizontal platform. This design allows the three pieces to be laminated easily either with a suitable glue, or glue may be used with screw nuts or by plastic "welding plugs". The laminated legs provide firm vertical support while the horizontal table will retain some flexibility. The removable and inversible tube block serves two purposes:

1. It helps to stabilize the rack structurally and reinforces a lower center of gravity.
2. It can be removed, inverted and laid on top of the collector tray of the rack. The 14 mm. holes then serve as a receptacle for the 2 ml. sample cups used for collecting 1 ml. of the MB fraction. During such collection, the different specimens processed can be transported in the tube block to the analyses area.

EXAMPLE 4

It is also possible to unplug the filter tip commonly used on many brands of filtered cigarettes or some facsimilie thereof employed as the entire column matrices for the column separation of CPK-MB isoenzyme. The linear cellulose fiber can either be converted to its DEAE (diethyl-amino-ethane) derivative by conventional means on existing filter plugs or a source of DEAE-cellulose can be directly obtained from various vendors and this raw material can be incorporated into cigarette filter tips. A useful cigarette filter tip has been found to have an appropriate configuration (30 mm. long, 10 mm in diameter). The DEAE-filter tip has the following advantages:

1. Low cost and rapid flow matrices.
2. The DEAE-filter tip is readily transported and sold as a disposable cartridge.
3. The DEAE-filter tip column, as a total package, is low cost to be considered a well as disposable.
4. The DEAE-filter tip column or the DEAE-filter tip cartridge can be shipped mailed, stored in dry form reducing inventory space, mailing cost and thus improving storability.

EXAMPLE 5

It has also been found possible to reuse the columns employed in this invention and which are a part thereof. That is to say, the columns can be recycled for carrying out the test. In addition, a continuous flow system can be employed. FIG. 3 shows the elution characteristics of repetitive runs using the same column for separation of CPK-MM from CPK-MB. FIG. 4 shows the elution profile of a newly employed column as compared to a repetitively used column. In each case, in FIGS. 3 and 4, the tubes identified as NOS. 7 and 8, Nos. 7 and 8 which comprise 2 cc. of the MB collection fraction does in fact contain the major portion of the MB peak.

Figure 5:
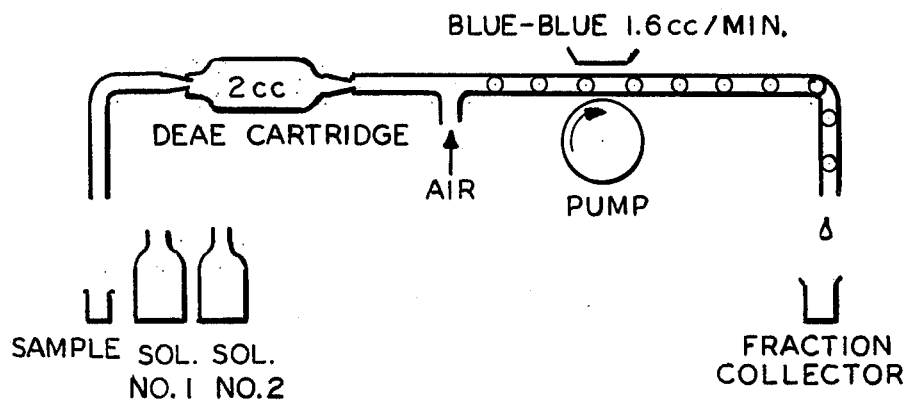
Figure 6:
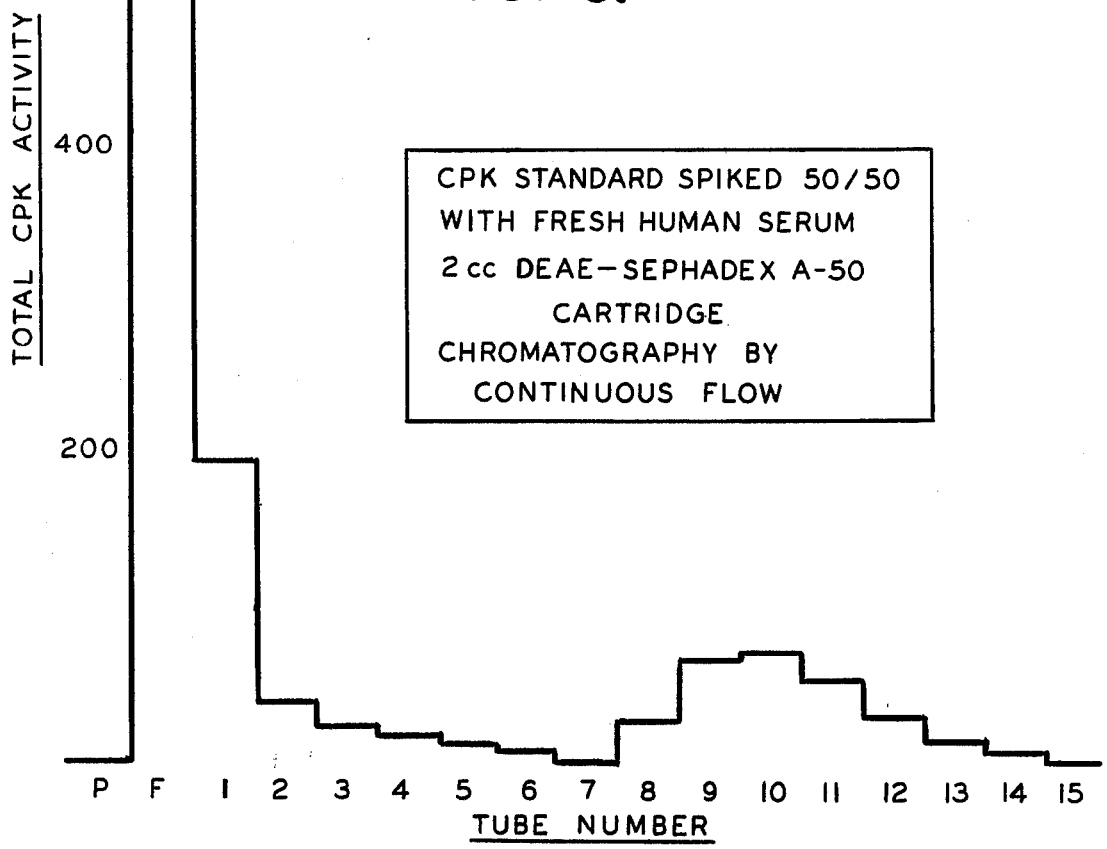

To show the use of a continuous flow system, FIGS. 5 and 6 are presented. In this embodiment, schematically shown in FIG. 5 the column or cartridge is placed proximate to a proporting pump such that the cartridge remains air free and receives in the following order, (1) a "slug" of sample, (2) Solution #1, and (3) solution #2, this procedure resulting in an elution pattern typically as shown on FIG. 6. It is to be noted that this pattern is substantially identical to the pattern of manual column separations shown in FIGS. 3 and 4.

EXAMPLE 6

It is believed important to provide a visual signal for the isolation of the MB fraction of CPK. Slight variations in column bed size, loading capacity, eluting buffers, temperature, and the like all add to slight changes in the eltuion profile of the MB fraction as obtained from time to time.

It has been found that the addition of green food coloring to Solution #1 provides a suitable marker for marking the MB fraction, and in addition a quite satisfactory quality control for the recycling procedure for re-using the DEAE-dextran column has been devised.

It has been found that conventional green food color is actually composed of a number of chromogens (i.e. green, blue and yellow). One drop of this green food color concentrate added to 1 liter of Solution #1 provides just sufficient color for marking purposes on conducting the test. When this green tinted Solution #1 is irrigated through the DEAE-dextran column all of the above pigments (chromogens) are adsorbed at the top of the column. The addition of 1.5 ml of serum onto such a column does not at all displace these three chromogens (green, blue and yellow). Upon further elution of the column with two or three aliquots of green tinted Solution #1, the chromogens continue to adsorb to the upper matrix of the column.

Upon priming the column with 1 ml of Solution #2, the band of chromogens being to descend the column. Upon eluting the column with another 2 ml of Solution #2, a band of the green chromogen elutes off the column together with the CPK-MB fraction. The blue and yellow pigment remain on the column matrices.

Upon the addition of 10-15 ml of Solution #2, the blue chromogen elutes off the column, indicating that the column is ready to be primed with Solution #1, or, as such, is ready for another CPK-MB run. A slight touch of yellow chromogen will continue to accumulate in the column with repeated cycles and this tendency serves to indicate when the column should be discarded, rather than recycled once more. The column will be throughly "jaundiced" after about 10 recycle steps which is a safe time finally to discard a recycled column.

Since the elution profile of the green chromogen contained in Solution #1 will vary with ionic strength, bed size, loading capacity, and the like, variables coincident to the MB fraction of CPK, this market serves as a valuable indicator of the overall inventive procedure. In addition, a futher advantage is that none of the pigments involved here in any way interferes with the CPK assay using the Rosalki substrate.

The use of green tinted Solution #1 is usable only in the DEAE-dextran columns, or hydrids made of DEAE-dextran with sea sand or inert glass beads. The use of other chromogens may be required for best results using other column matrices. The concept of using a visual marker for CPK-MB, however, that is, using colored indicators should preferably be employed. An alternate modification of this procedure, for example, is to add drop of diluted green food color to the serum just prior to the transfer of the assayed serum, into the test column.

EXAMPLE 7

This procedure for CPK-MB analysis on fresh human serum has been designed for detecting myocardial infarct (heart attack) as early as one half hour after the initial onset of the attack. Therefore, patients brought to the emergency room or the admission area of a large or a small community hospital may be expeditiously handled by the attending physician for immediate admission or extended observation. Therefore, the acute phase of infarct may be treated, rather than the documentation of an event 6 hours past and medical management may be facilitated by this laboratory datum.

This particular procedure has been tested in a double blind manner on 35 consecutive cases admitted to a special care unit under the direct supervison of a senior attending cardiologist, with the laboratory data performed personally by a full time Director of Clinical Biochemistry over a 2-month period. An additional 35 cases were also obtained from other in-patients or out-patients of the emergency room service during this period. The laboratory data fully corroborated the final clinical diagnosis and therefore sustains the term "100% sensitivity". In addition, since the invention procedure zeroes in on the slug of MB, a peak, rather than quantitative recovery is made. Thus patients suffering from infarct may be diagnosed as early as one half hour after onset and therefore the acute phase of the infarct can properly be managed by the attending physician.

The expression of CPK-MB is stated as an absolute number (mIu/ml) rather than a percentage of the total CPK acitivty. This approach is more logical, since the bulk of the CPK activity in the human body is skeletal and contains no MB except in muscle wastage disease. Thus, a patient who has a heart-attack, faints and falls down the stairs, will have a significant MB signal expressed by the invention method way, but an insignificant data when expressed as percentage of the total.

This kit has been formulated after a full 6-month service mode of Stat performance 7 days a week, 24 hours a day among three different shifts of technologists and is geared primarily to CPK assays using zero order kinetics.

What is claimed is:

1. A rapid laboratory test method for detection of heart attacks in human patients which comprises the steps of (1) passing a sample of 1.5 ml. of patient blood serum containing a green food color concentrate through a chromatographic column, (2) passing a first buffer solution of pH about 7.9 through said column, (3) passing an approximate total of 3.0 ml of a second buffer solution of pH about 6.9 in two portions through said column, (4) thereby isolating and identifying by means of said green food color concentrate the major portion of the creatine phosphokinease-MB isoenzyme from the resulting eluate, (5) continuing to pass said second buffer solution through said column, and (6) thereafter continuing to repeat, in consecutive order said steps 1, 2, 3, 4, and 5, thereby reusing the column for subsequent heart attack detection tests for separate individual patients.

2. The process of claim 1 in which said chromotographic column is used in continuous flow detection process rather than in distinct individual tests.

3. A diagnostic method for the rapid detection of heart attacks in human patients which comprises the steps of (1) passing a sample of patient blood serum containing a green food color concentrate through a chromatographic column, having about 1.5 to 2.5 cc bed volume (2) passing a first solution of pH about 7.9 containing NaCl and Tris buffer through said column, (3) passing a second solution of pH about 6.9 containing NaCl and Tris buffer through said column, and thereby (4) isolating and identifying by means of said food color concentrate the major portion of the creatine phosphokinase-MB isoenzyme from the resulting eluate.

4. The method of claim 3 in which the blood serum sample is passed through a high speed chromatographic column containing DEAE-dextran and having a cigarette filter tip located in the lower tip portion of said column.

5. The method of claim 3 in which only a major portion of said creatine-phosphokinase-MB isoenzyme fraction is isolated and identified.

6. The method of claim 3 in which the creatine-phosphokinase-MB isoenzyme fraction is quantitatively isolated and identified.

7. The method of claim 4 in which at least one of said three solutions contains a green food color concentrate adapted to function as an identifying code for the creatine phosphokinas-MB isoenzyme fraction.

8. The method of claim 7 in which the food color concentrate is included in the blood serum sample solution.

9. A rapid laboratory method for detection of heart attacks in human patients which comprises the steps of (1) passing an approximate 1.5 ml sample of patient blood serum containing a green food color concentrate through a 1.5 to 2.5 cc bed volume chromatographic column, (2) passing a first solution containing about 0.1 M NaCl and about 0.05 M Tris buffer through said column, (3) passing a second solution containing about 0.3 M NaCl and about 0.05 M Tris buffer through said column, and thereby (4) isolating and identifying the major portion of the creatine phosphokinase-MB isoenzyme from the rsulting eluate.

* * * * *